US011319263B1

(12) United States Patent
Alghannam et al.

(10) Patent No.: US 11,319,263 B1
(45) Date of Patent: May 3, 2022

(54) METHODS FOR LOW TEMPERATURE PRODUCTION OF 1-BUTENE (71) Applicant: Saudi Arabian Oil Company, Dhahran (SA)

(72) Inventors: Afnan Alghannam, Khobar (SA); Munir D. Khokhar, Dhahran (SA); Sohel K. Shaikh, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/190,908

(22) Filed: Mar. 3, 2021

(51) Int. Cl.
*C07C 5/25* (2006.01)
*C07C 11/08* (2006.01)
*B01J 37/02* (2006.01)
*B01J 35/10* (2006.01)
*B01J 37/08* (2006.01)
*B01J 29/70* (2006.01)
*B01J 23/30* (2006.01)
*B01J 6/00* (2006.01)

(52) U.S. Cl.
CPC ............. *C07C 5/2518* (2013.01); *B01J 6/001* (2013.01); *B01J 23/30* (2013.01); *B01J 29/70* (2013.01); *B01J 35/1023* (2013.01); *B01J 37/0201* (2013.01); *B01J 37/08* (2013.01); *C07C 11/08* (2013.01); *C07C 2523/30* (2013.01); *C07C 2529/70* (2013.01)

(58) Field of Classification Search
CPC ... B01J 6/001; B01J 23/30; B01J 29/70; B01J 35/1023; B01J 37/0201; B01J 37/08; C07C 5/2518; C07C 11/08; C07C 2523/30; C07C 2529/70
See application file for complete search history.

(56) References Cited

U.S. PATENT DOCUMENTS

| 21,858 | A | | 10/1858 | Swan |
| 3,752,864 | A | * | 8/1973 | Arganbright .......... C07C 5/2512 585/670 |
| 6,875,901 | B2 | | 4/2005 | Gartside et al. |
| 8,324,440 | B2 | | 12/2012 | Popp et al. |
| 8,586,813 | B2 | | 11/2013 | Ramachandran et al. |

OTHER PUBLICATIONS

Hua et al., "Transformation of 2-Butene into Propene on WO3/MCM-48: Methathesis and Isomerization of n-Butene", Catalysts, vol. 8, No. 585, 2018.
You et al., "Positional isomerization of butene-2 over nanoporous MCM-48 catalysts", J Nanosci Nanotechnol, vol. 11, 2007.

* cited by examiner

*Primary Examiner* — Youngsul Jeong
*Assistant Examiner* — Jason Y Chong
(74) *Attorney, Agent, or Firm* — Dinsmore & Shohl LLP (57) ABSTRACT

Methods of producing 1-butene from a 2-butene-containing feedstock include feeding a hydrocarbon feed comprising 2-butene to a reactor, the reactor containing an isomerization catalyst and contacting the hydrocarbon feed with the isomerization catalyst in the reactor at a temperature from 150° C. to 350° C. to produce an isomerization reaction effluent comprising 1-butene. Further, the isomerization catalyst comprises a MCM-48 catalyst with $WO_3$ incorporated into a silica framework of the MCM-48 catalyst.

15 Claims, 5 Drawing Sheets

METHODS FOR LOW TEMPERATURE PRODUCTION OF 1-BUTENE

BACKGROUND

Field

The present disclosure generally relates to methods of producing 1-butene and, more specifically, to isomerization catalysts and methods of using the isomerization catalyst to generate 1-butene at temperatures of less than 350° C.

Technical Background

In recent years, there has been a dramatic increase in the demand for 1-butene due to applications in the production of polyethylene, such as high density polyethylene (HDPE) and low density polyethylene (LDPE), and polybutenes. Currently, a majority of the 1-butene produced worldwide is produced by the dimerization of high-value feedstocks, such as ethylene, the dehydrogenation of butane, or separation from low-value $C_4$ feedstocks. These low-value $C_4$ feedstocks may be by-products or effluent streams from steam cracking units, which primarily produce ethylene, Fluid Catalytic Cracking (FCC) units, which primarily produce gasoline, or methyl tertiary butyl ether (MTBE) extraction units. However, these processes cannot respond adequately to the rapid increase in 1-butene demand. As a result, alternative methods to directly produce 1-butene have been developed and, in particular, methods of producing 1-butene from 2-butene-containing feedstocks.

The production of 1-butene from 2-butene-containing feedstocks can be accomplished through the isomerization of the 2-butene to 1-butene. Isomerization of 2-butene to produce 1-butene can better meet the growing demand for 1-butene. Isomerization can be accomplished by contacting 2-butene in the 2-butene-containing feedstock with an isomerization catalyst. However, conventional isomerization catalysts and, as a result, conventional 1-butene production processes are inefficient, often failing to convert a significant portion of 2-butenes and only resulting in a comparatively small 1-butene yield or require reaction at a significantly elevated temperature.

SUMMARY

Accordingly, there is an ongoing need for improved isomerization catalysts with increased catalytic activity at reactor temperatures less than 350° C. that, as a result, increases the conversion rate of 2-butene and the yield of 1-butene from a 2-butene isomerization process. The present disclosure is directed to methods of producing 1-butene from a 2-butene-containing feedstock through isomerization with the isomerization catalyst also disclosed in the present disclosure and at reactor temperatures of less than 350° C.

According to one or more embodiments of the present disclosure, a method of producing 1-butene from a 2-butene-containing feedstock may comprise feeding a hydrocarbon feed comprising 2-butene to a reactor, the reactor containing an isomerization catalyst; and contacting the hydrocarbon feed with the isomerization catalyst in the reactor at a temperature from 150° C. to 350° C. to produce an isomerization reaction effluent comprising 1-butene, wherein the isomerization catalyst comprises a MCM-48 catalyst with $WO_3$ incorporated into a silica framework of the MCM-48 catalyst.

Additional features and advantages of the technology described in the present disclosure will be set forth in the detailed description that follows and, in part, will be readily apparent to those skilled in the art from the description or recognized by practicing the technology as described in this disclosure.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
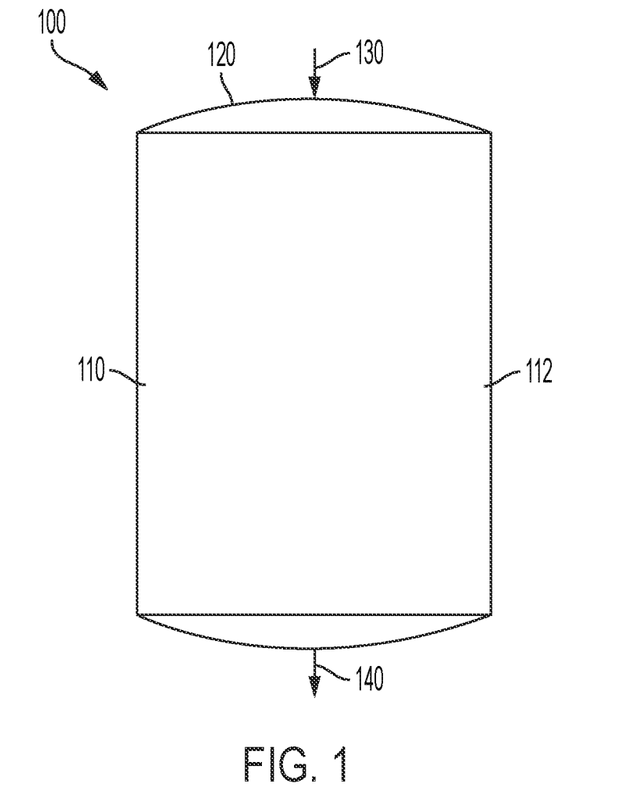
FIG. 1 schematically depicts a fixed bed continuous flow reactor including an isomerization reaction zone, according to one or more embodiments of the present disclosure.
Figure 2:
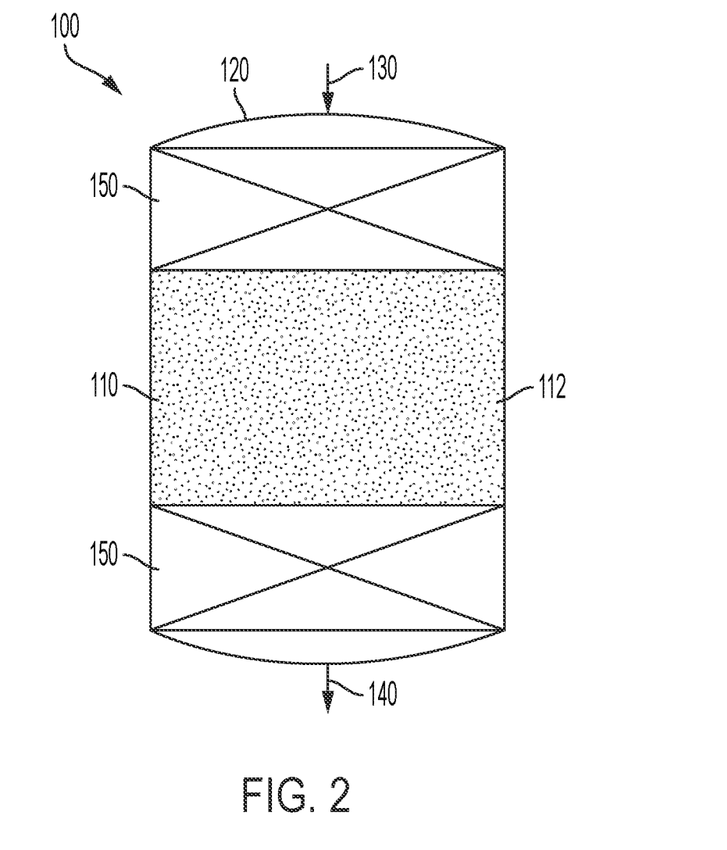
FIG. 2 schematically depicts another fixed bed continuous flow reactor including an isomerization reaction zone, according to one or more embodiments of the present disclosure.

For the purpose of describing the simplified schematic illustrations and descriptions of FIGS. 1 and 2, the numerous valves, temperature sensors, electronic controllers, and the like that may be employed and well-known to a person of ordinary skill in the art are not included. Further, accompanying components that are often included in typical chemical processing operations, carrier gas supply systems, pumps, compressors, furnaces, or other subsystems are not depicted. It should be understood that these components are within the spirit and scope of the present embodiments disclosed. However, operational components, such as those described in the present disclosure, may be added to the embodiments described in the present disclosure.

Arrows in the drawings refer to process streams. However, the arrows may equivalently refer to transfer lines, which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows that do not connect two or more system components may signify a product stream that exits the depicted system or a system inlet stream that enters the depicted system. Product streams may be further processed in accompanying chemical processing systems or may be commercialized as end products.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

Reference will now be made in greater detail to various embodiments, some embodiments of which are illustrated in the accompanying drawings.

DETAILED DESCRIPTION

The present disclosure is directed to methods of producing 1-butene from a 2-butene-containing feedstock through isomerization with an isomerization catalyst in accordance with the present disclosure. In particular, the present disclosure is directed to methods of producing 1-butene from a 2-butene-containing feedstock that include contacting the 2-butene-containing feedstock with the isomerization catalyst at a temperature from 150° C. to 350° C. to produce an isomerization reaction effluent that includes at least 1-butene. Further, the isomerization catalyst comprises a MCM-48 catalyst with $WO_3$ incorporated into a silica framework of the MCM-48 catalyst. The methods of producing 1-butene from a 2-butene-containing feedstock of the present disclosure may allow 1-butene to be generated at temperatures as low as 150° C. and avoids subsequent conversion of generated 1-butene to propene or other species through metathesis reaction.

As used throughout the present disclosure, the term "butene" or "butenes" may refer to compositions comprising one or more than one of 1-butene, trans-2-butene, cis-2-butene, isobutene, or mixtures of these isomers. As used throughout the present disclosure, the term "normal butenes" may refer to compositions comprising one or more than one of 1-butene, trans-2-butene, cis-2-butene, or mixtures of these isomers, and are substantially free of isobutene. As used in the present disclosure, the term "2-butene" may refer to trans-2-butene, cis-2-butene, or a mixture of these two isomers. As used in the present disclosure, the term "substantially free" of a component means less than 1 wt. % of that component in a particular portion of a catalyst, stream, or reaction zone. For example, a composition, which may be substantially free of isobutene, may comprise less than 1 wt. % of isobutene.

As shown in Reaction 1, the isomerization of 2-butene to 1-butene, and the isomerization of 1-butene to 2-butene, is an equilibrium reaction, as denoted by the bi-directional arrows with single heads. The isomerization of 2-butene and 1-butene may be achieved with an isomerization catalyst. As used in the present disclosure, the term "isomerization catalyst" may refer to a catalyst that promotes isomerization of alkenes, including, for example, isomerization of 2-butenes to 1-butene. Referring to Reaction 1, the isomerization reaction is not limited to these reactants and products; however, Reaction 1 provides a simplified illustration of the reaction methodology.

Reaction 1

In operation, a product stream comprising 1-butene may be produced from a feedstock containing 2-butene through isomerization by contacting the feedstock with an isomerization catalyst. Optionally, the isomerization reaction effluent, may be further processed, such as being contacted with a metathesis catalyst, a cracking catalyst, or both, to further utilize the 1-butene produced. The feedstock may comprise 1-butene, trans-2-butene, cis-2-butene, or combinations of these. The feedstock may further comprise other $C_1$-$C_6$ components. The presence of isobutene and other inert gases or non-olefinic hydrocarbons, such as n-butane, in the feedstock do not negatively affect the target isomerization reactions, and the amount of any side products formed as a result of their presence in the feedstock do not affect the overall yield of 1-butene. Although described in the present disclosure in the context of conducting isomerization between 2-butene and 1-butene, it is understood that the isomerization catalysts of the present disclosure and systems and methods of conducting isomerization using the isomerization catalysts may be useful for conducting other isomerization, such as isomerization between other olefins, or for conducting other functions, such as removing contaminants from a feed stream, for example.

Referring now to FIG. 1, a system for producing 1-butene from a feedstock containing 2-butene is depicted, the system being designated by reference number 100. The system 100 may include an isomerization reaction zone 110 or a plurality of isomerization reaction zones. The one or more isomerization reaction zones may be disposed within a single reactor 120 or in multiple reactors, which may be in series or in parallel. As depicted in FIG. 1, a feedstock 130 (hydrocarbon feedstock) may be introduced into the reactor 120, and an isomerization reaction effluent 140 may be passed out of the reactor 120. Accordingly, the feedstock 130 may be introduced into the reactor 120, passed through the isomerization reaction zone 110, and passed out of the reactor 120 as the isomerization reaction effluent 140.

As described previously in the present disclosure, the feedstock 130 may comprise 1-butene, cis-2-butene, trans-2-butene, or combinations of these. The feedstock 130 may comprise from 10 wt. % to 100 wt. % 2-butene (that is, cis-2-butene, trans-2-butene, or both) based on the total weight of the feedstock 130. For example, the feedstock 130 may comprise from 10 wt. % to 80 wt. %, from 10 wt. % to 60 wt. %, from 10 wt. % to 40 wt. %, from 10 wt. % to 20 wt. %, from 20 wt. % to 100 wt. %, from 20 wt. % to 80 wt. %, from 20 wt. % to 60 wt. %, from 20 wt. % to 40 wt. %, from 40 wt. % to 100 wt. %, from 40 wt. % to 80 wt. %, from 40 wt. % to 60 wt. %, from 60 wt. % to 100 wt. %, from 60 wt. % to 80 wt. %, or from 80 wt. % to 100 wt. % 2-butene based on the total weight of the feedstock 130. The feedstock 130 may comprise from 0 wt. % to 60 wt. % 1-butene based on the total weight of the feedstock 130. Additionally, the feedstock 130 may be substantially free of ethylene.

The feedstock 130 may comprise a raffinate stream. As used in the present disclosure, the term "raffinate" may refer to the residue $C_4$ stream from a naphtha cracking process or from a gas cracking process when components are removed (the C₄ stream typically containing, as its primary components, n-butane, 1-butene, 2-butene, isobutene, and 1,3-butadiene, and optionally some isobutane and said primary components together forming up to 99% or more of the C₄ stream). The feedstock 130 may comprise a raffinate-1 stream. As used in the present disclosure, the term "raffinate-1" may refer to the C₄ residual obtained after separation of 1,3-butadiene from a raffinate stream, and comprises mainly 2-butene, 1-butene, and isobutene, which may make up greater than or equal to 55 wt. % of the raffinate-1 stream. For example, the raffinate-1 stream may comprise from 10 wt. % to 30 wt. % of 2-butene, from 25 wt. % to 50 wt. % of 1-butene, and from 20 wt. % to 50 wt. % isobutene, based on the total weight of the raffinate-1 stream. The feedstock 130 may comprise a raffinate-2 stream. As used in the present disclosure, the term "raffinate-2" may refer to the C₄ residual obtained after separation of 1,3-butadiene and isobutene from a raffinate stream, and comprises mainly 2-butene, 1-butene, and n-butane, which may make up greater than or equal to 45 wt. % of the raffinate-2 stream. For example, the raffinate-2 stream may comprise from 20 wt. % to 60 wt. % of 2-butene, from 10 wt. % to 60 wt. % of 1-butene, and from 15 wt. % to 25 wt. % n-butane, based on the total weight of the raffinate-2 stream. The feedstock 130 may comprise a raffinate-3 stream. As used in the present disclosure, the term "raffinate-3" may refer to the C₄ residual obtained after separation of 1,3-butadiene, isobutene, and 1-butene from the C₄ raffinate stream, and comprises mainly 2-butene, n-butane, and unseparated 1-butene, which may make up greater than or equal to 40 wt. % of the raffinate-3 stream. For example, the raffinate-3 stream may comprise from 30 wt. % to 70 wt. % of 2-butene and from 10 wt. % to 30 wt. % of n-butane, based on the total weight of the raffinate-3 stream.

The isomerization reaction zone 110 may be maintained at an isomerization reaction temperature sufficient to promote the isomerization reactions between 2-butene and 1-butene in the feedstock 130. The isomerization reaction temperature may be from 150 degrees Celsius (° C.) to 350° C. For example, the isomerization reaction temperature may be from 150° C. to 300° C., from 150° C. to 250° C., from 200° C. to 350° C., from 200° C. to 300° C., or from 250° C. to 350° C. These temperature ranges may be sufficient to promote the isomerization reactions and, in particular, may be sufficient to promote the isomerization of 2-butene to 1-butene when utilizing the isomerization catalyst disclosed in the present disclosure. It will be appreciated that such temperature range is not expected to produce isomerization of 2-butene to 1-butene when traditional isomerization catalysts known to those skilled in the art are utilized. Without being bound by any particular theory, it is believed that these temperature ranges may shift the equilibrium of the isomerization reactions between 2-butene and 1-butene, such that the production of 1-butene is favored when isomerization catalysts in conformity with the present disclosure are utilized. Conversely, temperatures greater than 350° C. may shift the equilibrium of reactions such that 1-butene reacts with 2-butene to generate propene in a metathesis reaction as shown in Reaction 2 when isomerization catalysts in conformity with the present disclosure are utilized. Accordingly, these temperature ranges may increase the yield of 1-butene by system 100.

Reaction 2

Referring still to FIG. 1, the isomerization reaction zone 110 of the system 100 may include an isomerization catalyst 112. The isomerization catalyst 112 may be a MCM-48 catalyst with WO₃ incorporated into a silica framework of the MCM-48 catalyst in accordance with the present disclosure. The isomerization catalyst 112 may promote equilibration of the isomerization reactions between the 2-butene and 1-butene in the feedstock 130. When the feedstock 130 has a concentration of 2-butene greater than the equilibration concentration of 2-butene, the isomerization catalyst 112 may isomerize at least a portion of the 2-butene to 1-butene. Conversely, when the feedstock 130 has a concentration of 1-butene greater than the equilibrium concentration of 1-butene, the isomerization catalyst 112 may isomerize at least a portion of the 1-butene to 2-butene. The isomerization catalyst 112 may also shift the equilibrium of the isomerization reactions between 2-butene and 1-butene, such that the production of 1-butene is favored at equilibrium, or such that the production of 2-butene is favored at equilibrium, based on the operating conditions of the system 100. The isomerization reaction zone 110 may produce an isomerization effluent that may comprise 1-butene, cis-2-butene, trans-2-butene, or combinations of these.

Isomerization catalysts in accordance with the present disclosure include MCM-48 catalyst with WO₃ incorporated into a silica framework of the MCM-48 catalyst. In one or more embodiments, the WO₃ is incorporated into the silica framework of the MCM-48 catalyst by an incipient wetness impregnation method. The incipient wetness impregnation method may comprise adding ammonium metatungstate hydrate dissolved in water to the MCM-48 catalyst in a controlled manner to form an isomerization catalyst precursor. For example, the ammonium metatungstate hydrate solution may be added in a drop-wise manner to the MCM-48 catalyst to allow the ammonium metatungstate hydrate solution to permeate and be incorporated into the silica framework of the MCM-48 catalyst. The ammonium metatungstate hydrate is subsequently converted to WO₃ with further processing which results in WO₃ which is incorporated into the silica framework of the MCM-48 catalyst. Such catalyst may be alternatively referred to as WO₃/MCM-48. In various embodiments, the solution of ammonium metatungstate hydrate may be added at a volume and concentration such that the resulting WO₃/MCM-48 catalyst comprises 8 weight percentage (wt. %) to 12 wt. % of the WO₃. For example, the WO₃/MCM-48 catalyst may comprise 8 wt. % to 11 wt. %, 9 wt. % to 12 wt. %, 9 wt. % to 11 wt. %, 9.5 wt. % to 10.5 wt. %, or approximately 10 wt. % of the WO₃. The weight percentage of WO₃ in the WO₃/MCM-48 may be indicated in an abbreviated form of the name. For example, WO₃/MCM-48 catalyst with 10 wt. % of the WO₃ may be referenced as 10 wt. % WO₃/MCM-48.

After adding ammonium metatungstate hydrate dissolved in water to the MCM-48 catalyst in a controlled manner to form the isomerization catalyst precursor, the isomerization catalyst precursor may be dried and calcined to produce the isomerization catalyst. In one or more embodiments, the isomerization catalyst precursor may be dried through exposure to ambient air at ambient temperature through natural evaporative drying. In one or more embodiments, the isomerization catalyst precursor may be dried with vacuum drying. For example, the isomerization catalyst precursor may be placed in a vacuum oven at approximately 80° C. to draw out and expedite evaporation of water from the isomerization catalyst precursor dispersed throughout the silica framework of the MCM-48 catalyst. It will be appreciated that embodiments comprising the natural evaporative drying and embodiments comprising the vacuum drying may be combined to generate one or more embodiments with a hybrid drying method.

Calcination of the isomerization catalyst precursor converts the ammonium metatungstate hydrate dispersed through the silica framework of the MCM-48 catalyst into an oxidized form of $WO_3$. The formation of $WO_3$ within the silica framework of the MCM-48 catalyst is believed to increase the number of weak acid sites on the surface of the MCM-48 catalyst and thereby improve the catalytic performance.

The "calcination temperature" is a target average temperature to which the dried isomerization catalyst precursor is heated and at which the isomerization catalyst precursor is calcined over a period of time during the calcination process. The "ramping rate," as used in the present disclosure, is a rate at which the temperature of the magnesium oxide precipitant is increased from a starting temperature to the calcination temperature. The isomerization catalyst precursor may be placed in the calcination oven and the temperature of the calcination oven may be increased at the ramping rate to the calcination temperature. Then, the isomerization catalyst precursor may be maintained at the calcination temperature for a predetermined period of time. At the end of the predetermined period of time, the calcined isomerization catalyst precursor forming the isomerization catalyst may be allowed to slowly cool down to ambient temperature. Optionally, the isomerization catalyst precursor may be calcined a second time. The calcination temperature, ramping rate, and duration of the second calcination process may each be the same or different from the calcination temperature, ramping rate, and duration of the first calcination process.

The isomerization catalyst precursor may be calcined to form the isomerization catalyst in a calcination oven at a calcination temperature of from 450° C. to 650° C. For example, the isomerization catalyst precursor precipitant may be calcined in a calcination oven at a calcination temperature of from 450° C. to 600° C., from 450° C. to 550° C., from 450° C. to 500° C., from 500° C. to 650° C., from 500° C. to 600° C., from 500° C. to 550° C., from 550° C. to 650° C., from 550° C. to 600° C., or from 600° C. to 650° C. The ramping rate of the calcination process may be from 1 degree ° C./min to 4° C./min. For example, the ramping rate of the calcination process may be from 1° C./min to 3° C./min, from 1° C./min to 2.5° C./min, from 1° C./min to 2° C./min, from 1.5° C./min to 2° C./min, from 1.5° C./min to 4° C./min, from 1.5° C./min to 3° C./min, from 1.5° C./min to 2.5° C./min, from 1.5° C./min to 2° C./min, from 2° C./min to 4° C./min, from 2° C./min to 3° C./min, from 2° C./min to 2.5° C./min, from 2.5° C./min to 4° C./min, from 2.5° C./min to 3° C./min, or from 3° C./min to 4° C./min. The isomerization catalyst precursor may be calcined in the calcination oven for a duration of from 1 hour to 10 hours. For example, the isomerization catalyst precursor may be calcined in the calcination oven for a duration of from 1 hour to 8 hours, from 1 hour to 6 hours, from 1 hour to 4 hours, from 1 hour to 2 hours, from 2 hours to 10 hours, from 2 hours to 8 hours, from 2 hours to 6 hours, from 2 hours to 4 hours, from 4 hours to 10 hours, from 4 hours to 8 hours, from 4 hours to 6 hours, from 6 hours to 10 hours, or from 6 hours to 8 hours.

The isomerization catalyst precursor may be calcined to form the isomerization catalyst in a calcination oven at a calcination temperature in a two-step calcination process with an initial period at 150° C. to 350° C. followed by an increase to a second period at 450° C. to 650° C. For example, the isomerization catalyst precursor precipitant may be calcined in a calcination oven at a calcination temperature of from 150° C. to 300° C., from 150° C. to 250° C., from 10° C. to 200° C., from 200° C. to 350° C., from 200° C. to 300° C., from 200° C. to 250° C., from 250° C. to 350° C., from 250° C. to 300° C., or from 300° C. to 350° C. for the initial period and subsequently from 450° C. to 600° C., from 450° C. to 550° C., from 450° C. to 500° C., from 500° C. to 650° C., from 500° C. to 600° C., from 500° C. to 550° C., from 550° C. to 650° C., from 550° C. to 600° C., or from 600° C. to 650° C. during the second period. The ramping rate of the calcination process may be from 1 degree ° C./min to 4° C./min. For example, the ramping rate of the calcination process may be from 1° C./min to 3° C./min, from 1° C./min to 2.5° C./min, from 1° C./min to 2° C./min, from 1.5° C./min to 2° C./min, from 1.5° C./min to 4° C./min, from 1.5° C./min to 3° C./min, from 1.5° C./min to 2.5° C./min, from 1.5° C./min to 2° C./min, from 2° C./min to 4° C./min, from 2° C./min to 3° C./min, from 2° C./min to 2.5° C./min, from 2.5° C./min to 4° C./min, from 2.5° C./min to 3° C./min, or from 3° C./min to 4° C./min. The isomerization catalyst precursor may be calcined in the calcination oven for a duration of from 1 hour to 10 hours in each of the initial period and the second period. For example, the isomerization catalyst precursor may be calcined in the calcination oven for a duration of from 1 hour to 8 hours, from 1 hour to 6 hours, from 1 hour to 4 hours, from 1 hour to 2 hours, from 2 hours to 10 hours, from 2 hours to 8 hours, from 2 hours to 6 hours, from 2 hours to 4 hours, from 4 hours to 10 hours, from 4 hours to 8 hours, from 4 hours to 6 hours, from 6 hours to 10 hours, from 6 hours to 8 hours, or combinations thereof for each of the initial period and the second period.

The isomerization catalyst 112 in accordance with embodiments of the present disclosure may have a surface area of 550 square meters per gram ($m^2/g$) to 1000 $m^2/g$, as determined by the Brunauer Emmett-Teller (BET) method. For example, the isomerization catalyst 112 may have a surface area of from 550 $m^2/g$ to 900 $m^2/g$, from 600 $m^2/g$ to 800 $m^2/g$, from 700 $m^2/g$ to 1000 $m^2/g$, from 700 $m^2/g$ to 900 $m^2/g$, from 700 $m^2/g$ to 800 $m^2/g$, from 725 $m^2/g$ to 900 $m^2/g$, or from 725 $m^2/g$ to 825 $m^2/g$, as determined by the BET method. For comparison, in one or more embodiments, an isomerization catalyst in accordance with the present disclosure (10 wt. % $WO_3$/MCM-48) may have a surface area of 775.63 $m^2/g$ and an MCM-48 catalyst without incorporation of $WO_3$ may have a surface area of 917.68 $m^2/g$, each determined by the BET method. Such demonstrates a substantial reduction in the surface area of the isomerization catalyst 112 as a result of the incorporation of the $WO_3$.

The isomerization catalyst 12 resulting from the process of the present disclosure may have a cumulative pore volume of from 0.45 cubic centimeters per gram ($cm^3/g$) to 0.65 $cm^3/g$, as determined by the Barrett, Joyner, and Halenda (BJH) method. For example, the isomerization catalyst 112 may have a cumulative pore volume of from 0.45 cm$^3$/g to 0.60 cm$^3$/g, from 0.5 cm$^3$/g to 0.65 cm$^3$/g, from 0.5 cm$^3$/g to 0.6 cm$^3$/g, from 0.55 cm$^3$/g to 0.65 cm$^3$/g, or from 0.55 cm$^3$/g to 0.6 cm$^3$/g, as determined by the BJH method.

The isomerization catalyst 112 resulting from the process of the present disclosure may have an average pore width of from 0.6 nanometers (nm) to 1.8 nm, as determined by the BJH method. For example, the isomerization catalyst 112 may have an average pore width of from 0.6 nm to 1.6 nm, 0.6 nm to 1.4 nm, 0.6 nm to 1.25 nm, 0.8 nm to 1.6 nm, 0.8 nm to 1.4 nm, 0.81 nm to 1.25 nm, 1.1 nm to 1.6 nm, 1.1 nm to 1.4 nm, or 1.1 nm to 1.25 nm, as determined by the BJH method The isomerization catalyst 112 having these properties (that is, the previously described surface area, cumulative pore volume, average pore width, and average particle size) may have increased catalytic activity and activity at reactor temperatures less than 350° C. compared to commercially-available MCM-48 catalysts. As a result, the system 100 comprising the isomerization catalyst 112 may have an increased 1-butene yield compared to a system utilizing a conventional MCM-48 catalyst.

Referring now to FIG. 2, in embodiments, a fluid/solid separator 150 may be disposed downstream of the isomerization reaction zone 110, upstream of the isomerization reaction zone 110, or both. As used in the present disclosure, the term "fluid/solid separator" may refer to a fluid permeable barrier between catalyst beds that reduces or prevents solid catalyst particles in one catalyst bed from migrating from the reaction zone, while allowing for reactants and products to move through the separator. The fluid/solid separator 150 may be chemically inert and generally makes no contribution to the reaction chemistry. Inserting the fluid/solid separator 150 upstream or downstream of the isomerization reaction zone 110 may maintain the isomerization catalyst 112 in the isomerization reaction zone 110, and improve the isothermal stability of the isomerization reactions, which may lead to the decreased production of undesired by-products and increased yield of 1-butene.

Referring again to FIG. 1, various operating conditions are contemplated for contacting the feedstock 130 with the isomerization catalyst 112 in the isomerization zone 110. In embodiments, the feedstock 130 may contact the isomerization catalyst 112 in the isomerization zone 110 at a weight hourly space velocity (WHSV) of from 1 per hour (h$^{-1}$) to 10 h$^{-1}$. For example, the feedstock 130 may contact the isomerization catalyst 112 in the isomerization zone 110 at a space hour velocity of 1 h$^{-1}$ to 10 h$^{-1}$, 1 h$^{-1}$ to 5 h$^{-1}$, 1 h$^{-1}$ to 3.5 h$^{-1}$, 1.5 h$^{-1}$ to 3.5 h$^{-1}$, 1.5 h$^{-1}$ to 3 h$^{-1}$, or approximately 2.4 h$^{-1}$. Furthermore, the feedstock 130 may contact the isomerization catalyst 112 in the isomerization zone 110 at a pressure of from 1 bar to 3 bars. For example, the feedstock 130 may contact the isomerization catalyst 112 in the isomerization zone 110 at a pressure of from 1 bar to 2.5 bars, from 1 bar to 2 bars, from 1 bar to 1.5 bars, or from 1 bar to 1.25 bars. The feedstock 130 may also contact the isomerization catalyst 112 in the isomerization zone 110 at atmospheric pressure of approximately 1.01 bars.

Further, as previously indicated, the feedstock 130 may be contacted with the isomerization catalyst 112 in the isomerization zone 110 at a temperature of from 150 degrees Celsius (° C.) to 350° C. For example, the feedstock 130 may be contacted with the isomerization catalyst 112 in the reactor 120 of the system 100 at a temperature of from 150° C. to 300° C., from 150° C. to 250° C., from 200° C. to 350° C., from 200° C. to 300° C., or from 250° C. to 350° C.

Optionally, prior to the introduction of the feedstock 130 to the system 100, the isomerization catalyst 112 may be pretreated. For example, the isomerization catalyst 112 in the system 100 may be pretreated by passing a heated gas stream through the isomerization catalyst 112 for a pretreatment period. The gas stream may include one or more of an oxygen-containing gas, nitrogen gas ($N_2$), carbon monoxide (CO), hydrogen gas ($H_2$), a hydrocarbon gas, air, other inert gas, or combinations of these gases. The temperature of the heated gas stream may be from 400° C. to 700° C., from 400° C. to 650° C., from 400° C. to 600° C., from 500° C. to 700° C., from 500° C. to 650° C., from 500° C. to 600° C., from 525° C. to 600° C. or from 525° C. to 550° C. The pretreatment period may be from 10 hours to 30 hours, from 15 hours to 30 hours, from 20 hours to 30 hours, or from 22 hours to 26 hours. For example, the isomerization catalyst 112 in the system 100 may be pretreated with nitrogen gas at a temperature of 550° C. for a pretreatment period of approximately 24 hours before introducing the feedstock 130.

In one or more embodiments, at least 10% by weight of the 2-butene in the feedstock 130 is converted to 1-butene in the isomerization reaction effluent 140 when contacting the hydrocarbon feed with the isomerization catalyst in the reactor at a temperature from 150° C. to 350° C. For example, at least 10% by weight, at least 12% by weight, at least 14% by weight, or at least 16% by weight of the 2-butene in the feedstock 130 may be converted to 1-butene in the isomerization reaction effluent 140.

In one or more embodiments, at least 20% by weight of the cis-2-butene in the feedstock 130 is converted to isomers of the 2-butene in the isomerization reaction effluent 140 when contacting the hydrocarbon feed with the isomerization catalyst in the reactor at a temperature from 150° C. to 350° C. For example, at least 20% by weight, at least 25% by weight, at least 30% by weight, at least 35% by weight, or at least 40% by weight of the cis-2-butene in the feedstock 130 may be converted to constitutional isomers of the cis-2-butene in the isomerization reaction effluent 140. For clarity it is noted that conversion of the cis-2-butene in the feedstock 130 to isomers of the cis-2-butene in the isomerization reaction effluent 140 includes both stereoisomers and skeletal isomers of cis-2-butene which include a mix of trans-2-butene and 1-butene respectively.

Operation of the reactor 120 at a temperature from 150° C. to 350° C. allows the isomerization catalysts in accordance with the present disclosure to achieve isomerization of 2-butenes without metathesis reaction of the same into propene or other non-butene products. In one or more embodiments, less than 2% by weight of the feedstock 130 is converted to $C_1$-$C_3$ hydrocarbons in the isomerization reaction effluent 140 when contacting the hydrocarbon feed with the isomerization catalyst in the reactor at a temperature from 150° C. to 350° C. For example, less than 2% by weight, less than 1% by weight, less than 0.5% by weight, or less than 0.25% by weight of the feedstock 130 is converted to $C_1$-$C_3$ hydrocarbons in the isomerization reaction effluent 140. As such, in one or more embodiments, the feedstock 130 may be considered substantially free of $C_1$-$C_3$ hydrocarbons or substantially free of $C_1$-$C_3$ hydrocarbons in excess of those initially provided in the feedstock 130.

In one or more embodiments, methods of producing 1-butene from a 2-butene-containing feedstock in accordance with the present disclosure are achieved with the reactor 120 free of a second isomerization catalyst. Specifically, embodiments of the present disclosure may produce 1-butene from a 2-butene-containing feedstock in the reactor 120 at a temperature from 150° C. to 350° C. with the only catalyst provided in the reactor 120 being the MCM-48 catalyst with $WO_3$ incorporated into a silica framework of the MCM-48 catalyst in accordance with the present disclosure.

In one or more embodiments, methods of producing 1-butene from a 2-butene-containing feedstock in accordance with the present disclosure are achieved with the reactor 120 explicitly free of MgO based catalysts. Specifically, embodiments of the present disclosure may produce 1-butene from a 2-butene-containing feedstock in the reactor 120 at a temperature from 150° C. to 350° C. with the no MgO based catalyst provided in the reactor 120 to function as an isomerization catalyst.

EXAMPLES

The various embodiments of isomerization catalysts, methods of making the isomerization catalysts, and methods of using the isomerization catalyst in the production of 1-butene will be further clarified by the following examples. The examples are illustrative in nature, and should not be understood to limit the subject matter of the present disclosure.

Inventive Example 1—$WO_3$/MCM-48

A MCM-48 catalyst with $WO_3$ incorporated into the silica framework of the MCM-48 catalyst was prepared in accordance with incipient wetness impregnation methods. Specifically, 0.177 grams (g) of ammonium metatungstate hydrate (99.9+%, Strem chemicals Inc.) was dissolved in 1.5 g of deionized water. The resulting ammonium metatungstate hydrate solution was then added drop by drop to 1.5 g of MCM-48 (Sigma-Aldrich). The MCM-48 catalyst with incorporated ammonium metatungstate hydrate solution was then dried overnight in a preheated oven at 80° C. to form a dried catalyst precursor. The dried catalyst precursor was then calcined in a calcination oven under air at a temperature of 250° C. for 3 hours and then increased to a temperature of 550° C. for a period of 8 hours to form the isomerization catalyst in accordance with present disclosure. The temperature increases from 250° C. to 550° C. was completed at a ramping rate of 1° C./min. The resulting catalyst represents a 10 wt. % $WO_3$/MCM-48 catalyst. The isomerization catalyst prepared according to the above-described method is referred to subsequently as Example 1 ($WO_3$/MCM-48).

Comparative Example 2—Commercially Available MCM-48

Comparative Example 2 (MCM-48) represents the MCM-48 (Sigma-Aldrich) utilized in the production of Example 1 without further processing.

Evaluation of Isomerization Catalyst Structures

Figure 3:
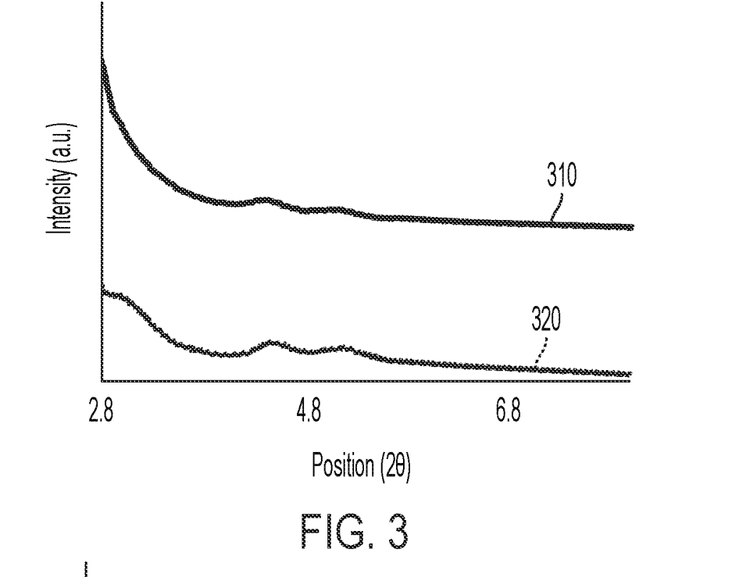
FIG. 3 graphically depicts the X-ray diffraction (XRD) profiles in the range of 2.8°-8° of isomerization catalysts, according to one or more embodiments of the present disclosure.
Figure 4:
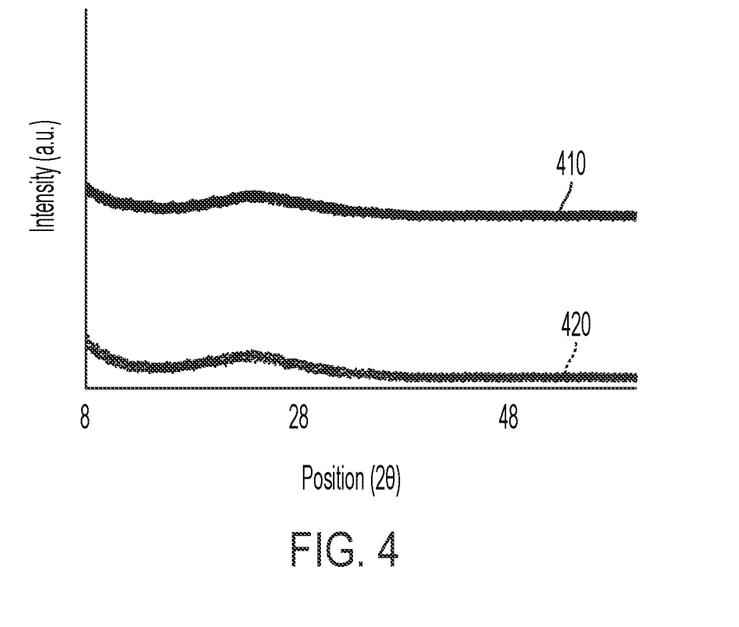
FIG. 4 graphically depicts the X-ray diffraction (XRD) profiles in the range of 8°-50° of isomerization catalysts, according to one or more embodiments of the present disclosure.

The crystallographic structures of the catalysts of Examples 1 and 2 were obtained from the measured XRD profiles of the catalysts (Bruker D4 Endeavor, $CuK_\alpha$ radiation, Ni filter). The XRD profiles of the catalyst of Inventive Example 1 (310/410) and the catalyst of Comparative Example 2 (320/420) are depicted in FIGS. 3 and 4. To aid in distinguishing between Inventive Example 1 ($WO_3$/MCM-48) and Comparative Example 2 (MCM-48), the XRD patterns were divided into two segments (2theta 2.8° through 8°) and (2theta 8° through 50°) in FIG. 3 and FIG. 4 respectively. It is noted that the catalysts of both Inventive Example 1 and Comparative Example 2 exhibited a $SiO_2$ characteristic peak located at 2theta of 24°. A comparison of the XRD patterns between Inventive Example 1 and Comparative Example 2 demonstrates that upon incorporating $WO_3$ into the MCM-48 framework as done in Inventive Example 1, the intensity of the MCM-48 peaks are slightly reduced with undetected $WO_3$ peaks indicating high dispersion of $WO_3$ in the silica framework of the MCM-48. These peaks occur at 2theta of 3.7° to 4.9° and 23° to 24°.

Figure 5:
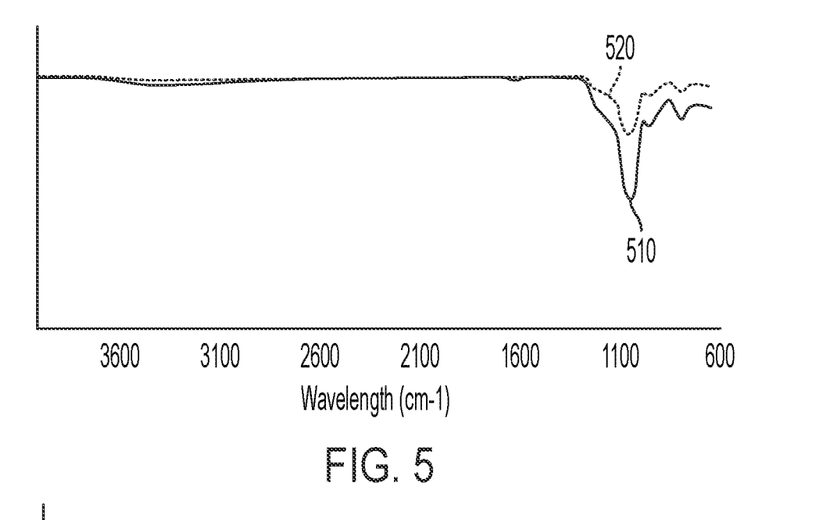
FIG. 5 graphically depicts the Fourier-transform infrared spectroscopy (FTIR) spectra of isomerization catalysts, according to one or more embodiments of the present disclosure.

The structures of the catalysts of Examples 1 and 2 were also analyzed with measured Fourier-transform infrared spectroscopy (FTIR) spectra. The FTIR spectra of the catalyst of Inventive Example 1 (510) and the catalyst of Comparative Example 2 (520) are depicted in FIG. 5. The spectra show the appearance of an OH stretching band (2900-3600 $cm^{-1}$) that corresponds to incorporation of acidic sites to the surface of Inventive Example 1. Further, it is noted that the addition of $WO_3$ into the framework is indicated by the presence of small W=O bands (below 1300 $cm^{-1}$). It may be appreciated that a shoulder peak near 950 value corresponds to $WO_3$ species being supported on MCM-48. The addition of the acidic sites to the surface of Inventive Example 1 are believed to be at least partially responsible for the increased 1-butene production and selectivity demonstrated by Inventive Example 1 when matched to Comparative Example 2 which lacks $WO_3$ and the associated increased acidic sites.

Evaluation of Catalyst Properties

The mechanical properties of the catalyst of Inventive Example 1, as well as the catalyst of Comparative Example 2, were determined and provided in Table 1. In particular, the surface areas of the catalysts were determined by the Brunauer Emmett-Teller (BET) method, the cumulative volume of pores and the average pore width were determined by the Barrett, Joyner, and Halenda (BJH) method, and the average particle sizes were calculated by the Scherrer equation. As shown by Table 1, the catalyst of Inventive Example 1 had a slightly reduced surface area and pore volume compared to the catalysts of Comparative Example 2. As shown by the results of the subsequently presented Catalytic Performance Evaluations, the catalyst of Inventive Example 1 also resulted in greater 1-butene yields than Comparative Example 2 at reactor temperatures below 350° C. This may suggest that the incorporation of $WO_3$ within the silica framework of the MCM-48 catalyst in accordance with Inventive Example 1 may directly contribute to improved isomerization catalytic activity at reactor temperatures of less than 350° C.

TABLE 1

Catalyst Mechanical Properties

| Catalyst | Surface Area ($m^2$/g) | Cumulative Volume of Pores ($cm^3$/g) | Average Pore Width (Å) | Average Particle Size (Å) |
| --- | --- | --- | --- | --- |
| Inventive Example 1 (10 wt. % $WO_3$/MCM-48) | 917.68 | 0.584 | 12.72 | 1450 |
| Comparative Example 2 (Commercially-Available MCM-48) | 775.63 | 0.465 | 11.98 | 1286 |

The acidity of the catalyst of Inventive Example 1 and the catalyst of Comparative Example 2 were determined in accordance with ammonia temperature-programmed desorption ($NH_3$-TPD) and are provided in Table 1. The $NH_3$-

Figure 6:
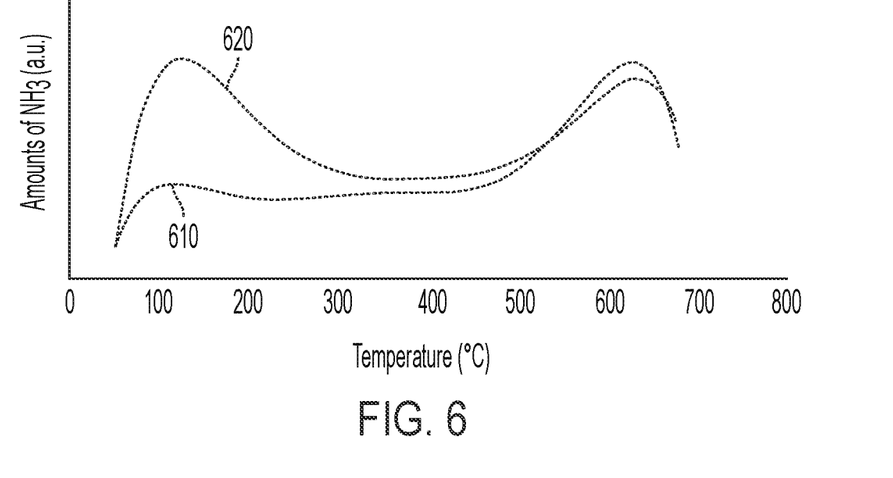
FIG. 6 graphically depicts the ammonia temperature programmed desorption ($NH_3$-TPD) profiles of isomerization catalysts, according to one or more embodiments of the present disclosure.

TPD profiles of the catalyst of Inventive Example 1 (610) and the catalyst of Comparative Example 2 (620) are depicted in FIG. 6. An analysis of FIG. 6 illustrates creation of weak acidic sites in $WO_3$/MCM-48 (Inventive Example 1) as indicated by the presence of a lower peak for Inventive Example 1 than Comparative Example 2 within the 100-250° C. desorption range.

TABLE 2

Catalyst Acid Properties

| Catalyst | $NH_3$-TPD Total Acidity (μmol/g) |
|---|---|
| Inventive Example 1 (10 wt. % $WO_3$/MCM-48) | 958.29 |
| Comparative Example 2 (Commercially-Available MCM-48) | 172.25 |

Evaluation of Catalyst Performance

The catalysts of Inventive Example 1 and Comparative Example 2, were tested for activity and selectivity for isomerizing a butene-containing feed to 1-butene in a fixed-bed continuous flow reactor, such as the reactor depicted in FIG. 2, at atmospheric pressure. A fixed amount of 0.1 g of each catalyst was pressed and sieved to a desired particle size in the range of 212-300 microns (μm), and was packed into a reactor tube. Layers of silicon carbide were positioned both upstream and downstream of the catalysts in order to ensure that the catalysts remained within the desired isothermal range.

Each reactor was first heated to 120° C. under nitrogen at a flow rate of 120 milliliters per minute (mL/min) and argon at a flow rate of 6 mL/min for 24 hours in order to ensure slow moisture desorption from the catalysts and identify any potential gas leaks from the reactors. The catalysts were then activated under nitrogen at 550° C. and a flow rate of 120 mL/min for 24 hours. The reactors were then cooled to predetermined reactor temperature under nitrogen before a feedstock of cis-2-butene was passed through the reactors at a flow rate of 0.004 grams per minute (g/min) and a weight hourly space velocity (WHSV) of 2.4 per hour ($h^{-1}$). Testing was completed as reactor temperatures of 100° C., 200° C., 300° C., 400° C., and 500° C. in subsequent trials to provided comparative temperature data. Testing was completed at 100° C., 200° C. 400° C., and 500° C. for 12 hours. Testing was completed at 300° C. for 48 hours to check for deactivation of the catalyst. It is noted that significant deactivation was not noted. Quantitative analysis of the products for each reactor was performed using a gas chromatograph (commercially available as Agilent GC-7890B) with a thermal conductivity detector (TCD) and two flame ionization detectors (FID).

The resulting products, as determined via gas chromatography, at each of the reactor temperatures of 100° C., 200° C., 300° C., 400° C., and 500° C. are provided in Tables 3 and 4 for Inventive Example 1 and Comparative Example 2 respectively. The product yields are provided as an average yield of the 16 individual reactors run in parallel.

TABLE 3

Average Catalytic Performance of Inventive Example 1 ($WO_3$/MCM-48)

| Temperature (° C.) | Product Yield (wt. %) | | | | | | | | | |
|---|---|---|---|---|---|---|---|---|---|---|
| | Ethylene | Propane | Propene | cis-2-butene | trans-2-butene | 1-butene | i-butene | $C_5$ | $C_6$ | Heavies ($C_7$+) |
| 100 | 0 | 0 | 0.00 | 99.14 | 0.54 | 0.12 | 0 | 0 | 0 | 0.0 |
| 200 | 0 | 0 | 0.01 | 56.13 | 30.03 | 12.21 | 0 | 0.06 | 0 | 0.0 |
| 300 | 0 | 0 | 0.15 | 37.36 | 43.72 | 17.64 | 0.06 | 0.30 | 0.02 | 0.00 |
| 400 | 0.61 | 0.01 | 12.02 | 20.64 | 28.15 | 16.02 | 0.38 | 16.78 | 4.04 | 1.37 |
| 500 | 3.62 | 0.30 | 23.88 | 10.19 | 12.15 | 8.78 | 1.39 | 20.39 | 10.37 | 8.66 |

TABLE 4

Average Catalytic Performance of Comparative Example 2 (MCM-48)

| Temperature (° C.) | Product Yield (wt. %) | | | | | | | | | |
|---|---|---|---|---|---|---|---|---|---|---|
| | Ethylene | Propane | Propene | cis-2-butene | trans-2-butene | 1-butene | i-butene | $C_5$ | $C_6$ | Heavies ($C_7$+) |
| 100 | 0 | 0 | 0 | 99.72 | 0.24 | 0.04 | 0 | 0 | 0 | 0 |
| 200 | 0 | 0 | 0 | 99.71 | 0.14 | 0.05 | 0 | 0 | 0 | 0 |
| 300 | 0 | 0 | 0.02 | 99.33 | 0.29 | 0.24 | 0.07 | 0.0 | 0 | 0.05 |
| 400 | 0 | 0 | 0.03 | 87.59 | 6.22 | 6.03 | 0.07 | 0.0 | 0.0 | 0.06 |
| 500 | 0.03 | 0 | 0.08 | 72.09 | 14.46 | 13.14 | 0.11 | 0.03 | 0.0 | 0.06 |

The catalytic performance of MCM-48 (Comparative Example 2) and $WO_3$/MCM-48 (Inventive Example 1) for 2-butene isomerization at 1 atmosphere (atm) and temperatures in the range of 100-500° C. is provided in Tables 3 and 4 which provide product distribution for each catalyst at each of 100° C., 200° C., 300° C., 400° C., and 500° C. It is initially noted that at 100° C., both Inventive Example 1 and Comparative Example 2 are inactive toward 2-butene isomerization reaction with Inventive Example 1 producing less than 0.12 wt. % of 1-butene and Comparative Example 2 producing no measurable 1-butene. Raising the temperature to 200° C. activates Inventive Example 1, but Comparative Example 2 remains inactive. Specifically, the 1-butene yield of Comparative Example 2 remains below any measurable level while Inventive Example 1 (10 wt. % $WO_3$ loading on MCM-48) achieves a 1-butene yield of 12.21 wt. % with conversion of 44 wt. % of the cis-2-butene to its isomers. Such increase in isomerization activity is unexpected by one skilled in the art. Upon increase to 300° C., the isomerization activity of Inventive Example 1 is further enhanced by 44.5% and its thermal stability is also improved. Reaction at 300° C. results in 97.3% of products which are 1-butene and 2-butene isomers with a limited remaining balance of impurities such as propene, $C_5$, and $C_6$.

Analysis of the product streams of Tables 3 and 4 demonstrates a shift in catalytic performance as the reactor temperature is increased to 400° C. and higher. Specifically, metathesis reaction is favored by Inventive Example 1 as the reactor temperature reaches 400° C. Specifically, at 400° C., 1-butene yield with Inventive Example 1 begins to decline and propene yield is increased to 12 wt %. Propene production is maintained during an operation time of 50 hours with no loss in activity. Raising the reaction temperature of the reactor further to 500° C. results in an increase in propene production (23.9 wt. %) through reacting 1-butene with 2-butene resulting in a commensurate reduction in 1-butene yield (8.78 wt. %). Such shift in the composition of the reactor effluent stream upon reaching a reactor operating temperature of 400° C. demonstrates that operation of a reactor with Inventive Example 1 ($WO_3$/MCM-48) at a temperature of less than 400° C. is critical to utilization of such catalyst as an isomerization catalyst and more specifically to generate maximal 1-butene yield.

Figure 7:
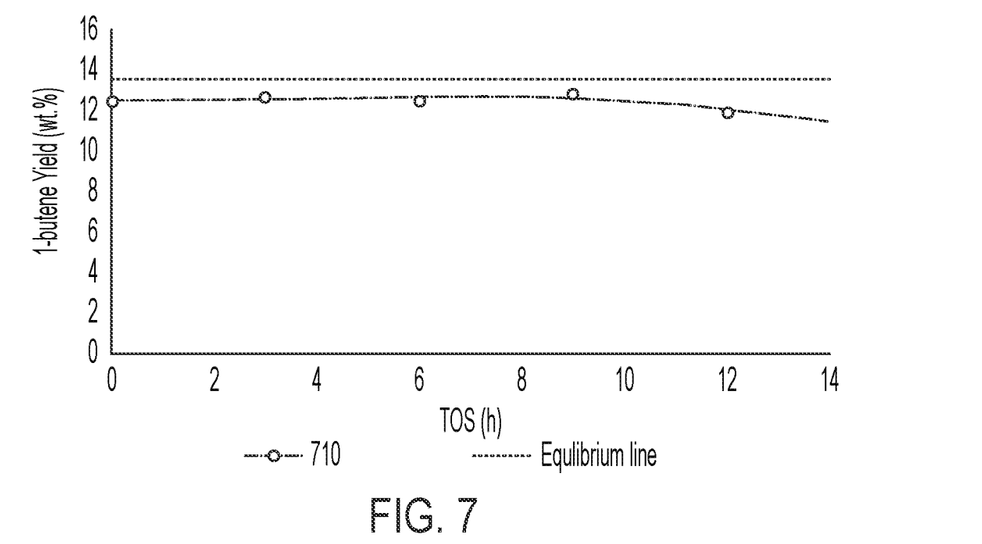
FIG. 7 graphically depicts the 1-butene yield (y-axis) as a function of time-on-stream (x-axis) obtained from a reactor for isomerizing a butene-containing feedstock, according to one or more embodiments of the present disclosure.

The 1-butene yield (wt. %) as a function of time-on-stream (TOS) for reactors comprising the catalyst of Inventive Example 1 (710) operated at a reactor temperature of 200° C. is depicted in FIG. 7. As shown by FIG. 7, Inventive Example 1 ($WO_3$/MCM-48) maintained its catalytic performance during the tested operating period of 14 hours without significant reduction in 1-butene yield. It is noted that the equilibrium line represents equilibrium at non-catalytic conditions.

Figure 8:
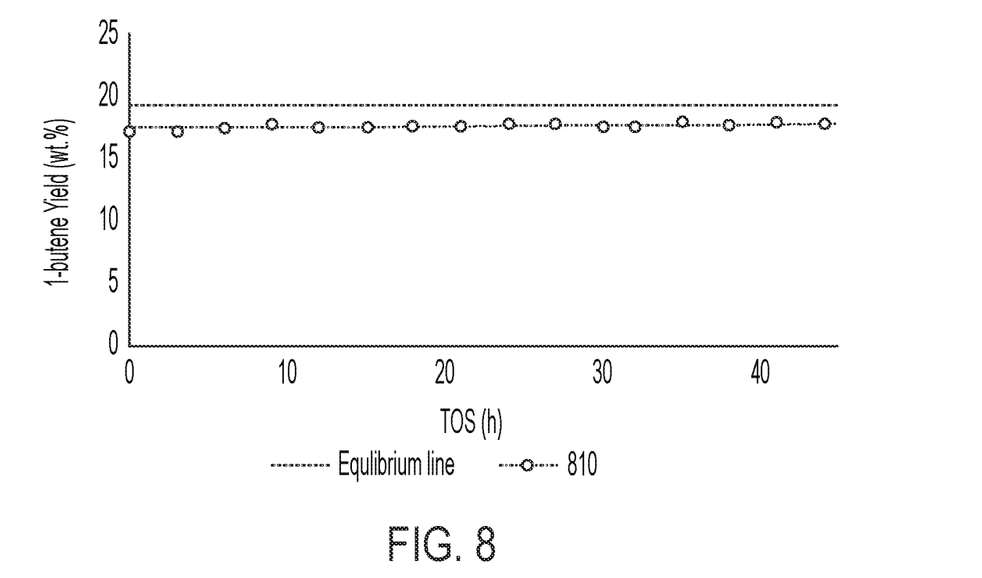
FIG. 8 graphically depicts the 1-butene yield (y-axis) as a function of time-on-stream (x-axis) obtained from a reactor for isomerizing a butene-containing feedstock, according to one or more embodiments of the present disclosure.

The 1-butene yield (wt. %) as a function of TOS for reactors comprising the catalyst of Inventive Example 1 (810) operated at a reactor temperature of 300° C. is similarly depicted in FIG. 8. As shown by FIG. 8, Inventive Example 1 ($WO_3$/MCM-48) maintained its catalytic performance during the tested operating period of 50 hours without significant reduction in 1-butene yield. It is noted that the equilibrium line represents equilibrium at non-catalytic conditions.

It will be apparent to those skilled in the art that various modifications and variations can be made without departing from the spirit or scope of the disclosure. Since modifications, combinations, sub-combinations and variations of the disclosed embodiments incorporating the spirit and substance of the disclosure may occur to persons skilled in the art, the scope of the disclosure should be construed to include everything within the scope of the appended claims and their equivalents.

In a first aspect of the present disclosure, a method of producing 1-butene from a 2-butene-containing feedstock may comprise feeding a hydrocarbon feed comprising 2-butene to a reactor, the reactor containing an isomerization catalyst; and contacting the hydrocarbon feed with the isomerization catalyst in the reactor at a temperature from 150° C. to 350° C. to produce an isomerization reaction effluent comprising 1-butene, wherein the isomerization catalyst comprises a MCM-48 catalyst with $WO_3$ incorporated into a silica framework of the MCM-48 catalyst.

A second aspect of the present disclosure may comprise the method of the first aspect where the reactor is operated at 200 to 300° C. to produce the isomerization reaction effluent comprising 1-butene.

A third aspect of the present disclosure may comprise the method of the first or second aspect where the BET surface area of the isomerization catalyst is 600 $m^2$/g to 1000 $m^2$/g.

A fourth aspect of the present disclosure may comprise the method of any of the first through third aspects where the average pore width in accordance with BJH Adsorption of the isomerization catalyst is 5 Å to 20 Å.

A fifth aspect of the present disclosure may comprise the method of any of the first through fourth aspects where at least 10% by weight of the 2-butene in the hydrocarbon feed is converted to 1-butene in the isomerization reaction effluent.

A sixth aspect of the present disclosure may comprise the method of any of the first through fifth aspects where at least 20% by weight of cis-2-butene in the hydrocarbon feed is converted to isomers of the cis-2-butene in the isomerization reaction effluent.

A seventh aspect of the present disclosure may comprise the method of any of the first through fifth aspects where at least 35% by weight of cis-2-butene in the hydrocarbon feed is converted to isomers of the cis-2-butene in the isomerization reaction effluent.

An eighth aspect of the present disclosure may comprise the method of any of the first through seventh aspects where less than 2% by weight of the hydrocarbon feed is converted to C1-C3 hydrocarbons in the isomerization reaction effluent.

A ninth aspect of the present disclosure may comprise the method of any of the first through eighth aspects where the isomerization catalyst comprises 5 to 15 wt % of the $WO_3$.

A tenth aspect of the present disclosure may comprise the method of any of the first through eighth aspects where the isomerization catalyst comprises 8 to 12 wt % of the $WO_3$.

An eleventh aspect of the present disclosure may comprise the method of any of the first through tenth aspects where the $WO_3$ is incorporated into the silica framework of the MCM-48 catalyst by an incipient wetness impregnation method.

A twelfth aspect of the present disclosure may comprise the method of the eleventh aspect where the incipient wetness impregnation method comprises adding ammonium metatungstate hydrate dissolved in water to the MCM-48 catalyst in a controlled manner to form an isomerization catalyst precursor; drying the isomerization catalyst precursor; and calcining the isomerization catalyst precursor which has been dried at 450° C. to 650° C. for at least 1 hour.

A thirteenth aspect of the present disclosure may comprise the method of the twelfth aspect where calcining the isomerization catalyst precursor which has been dried comprises an initial period at 150° C. to 350° C. followed by an increase to 450° C. to 650° C. at a ramp rate of 1° C. per minute.

A fourteenth aspect of the present disclosure may comprise the method of any of the first through thirteenth aspects where the 2-butene in the hydrocarbon feed is provided to the isomerization catalyst in the reactor at a weight hourly space velocity of from 1 $h^{-1}$ to 10 $h^{-1}$.

A fifteenth aspect of the present disclosure may comprise the method of any of the first through thirteenth aspects where the 2-butene in the hydrocarbon feed is provided to the isomerization catalyst in the reactor at a weight hourly space velocity of from 1 $h^{-1}$ to 3.5 $h^{-1}$.

A sixteenth aspect of the present disclosure may comprise the method of any of the first through fifteenth aspects where the reactor is free of MgO based catalyst.

A seventeenth aspect of the present disclosure may comprise the method of any of the first through sixteenth aspects where the reactor is free of a second isomerization catalyst.

It should now be understood that various aspects of the present disclosure are described and such aspects may be utilized in conjunction with various other aspects.

It is noted that one or more of the following claims utilize the term "where" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated or included quantitative values of a given property are contemplated in this disclosure. It should be appreciated that compositional ranges of a chemical constituent in a stream or in a reactor should be appreciated as containing, in some embodiments, a mixture of isomers of that constituent. For example, a compositional range specifying butene may include a mixture of various isomers of butene. It should be appreciated that the examples supply compositional ranges for various streams, and that the total amount of isomers of a particular chemical composition can constitute a range.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the appended claims should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A method of producing 1-butene from a 2-butene-containing feedstock, the method comprising:
    feeding a hydrocarbon feed comprising 2-butene to a reactor, the reactor containing an isomerization catalyst; and
    contacting the hydrocarbon feed with the isomerization catalyst in the reactor at a temperature from 150° C. to 350° C. to produce an isomerization reaction effluent comprising 1-butene,
    wherein the isomerization catalyst comprises a MCM-48 catalyst with $WO_3$ incorporated into a silica framework of the MCM-48 catalyst, where the average pore width in accordance with BJH Adsorption of the isomerization catalyst is 6 Å to 18 Å.

2. The method of claim 1 where the reactor is operated at 200 to 300° C. to produce the isomerization reaction effluent comprising 1-butene.

3. The method of claim 1 where the BET surface area of the isomerization catalyst is 550 $m^2$/g to 1000 $m^2$/g.

4. The method of claim 1 where at least 10% by weight of the 2-butene in the hydrocarbon feed is converted to 1-butene in the isomerization reaction effluent.

5. The method of claim 1 where at least 20% by weight of cis-2-butene in the hydrocarbon feed is converted to isomers of the cis-2-butene in the isomerization reaction effluent.

6. The method of claim 1 where at least 35% by weight of cis-2-butene in the hydrocarbon feed is converted to isomers of the cis-2-butene in the isomerization reaction effluent.

7. The method of claim 1 where less than 2% by weight of the hydrocarbon feed is converted to $C_1$-$C_3$ hydrocarbons in the isomerization reaction effluent.

8. The method of claim 1 where the isomerization catalyst comprises 8 to 12 wt. % of the $WO_3$.

9. The method of claim 1 where the $WO_3$ is incorporated into the silica framework of the MCM-48 catalyst by an incipient wetness impregnation method.

10. The method of claim 9 where the incipient wetness impregnation method comprises:
    adding ammonium metatungstate hydrate dissolved in water to the MCM-48 catalyst in a controlled manner to form an isomerization catalyst precursor;
    drying the isomerization catalyst precursor; and
    calcining the isomerization catalyst precursor which has been dried at 450° C. to 650° C. for at least 1 hour.

11. The method of claim 10 where calcining the isomerization catalyst precursor which has been dried comprises an initial period at 150° C. to 350° C. followed by an increase to 450° C. to 650° C. at a ramp rate of 1° C. per minute.

12. The method of claim 1 where the 2-butene in the hydrocarbon feed is provided to the isomerization catalyst in the reactor at a weight hourly space velocity of from 1 $h^{-1}$ to 10 $h^{-1}$.

13. The method of claim 1 where the 2-butene in the hydrocarbon feed is provided to the isomerization catalyst in the reactor at a weight hourly space velocity of from 1 $h^{-1}$ to 3.5 $h^{-1}$.

14. The method of claim 1 where the reactor is free of MgO based catalyst.

15. The method of claim 1 where the reactor is free of a second isomerization catalyst.

* * * * *